United States Patent [19]

Zecchino et al.

[11] Patent Number: 5,468,471
[45] Date of Patent: Nov. 21, 1995

[54] TITANIUM DIOXIDE DISPERSIONS, COSMETIC COMPOSITIONS AND METHODS FOR USING SAME

[75] Inventors: Julius R. Zecchino, Closter, N.J.; Steven Messin, Plainview, N.Y.; Cathleen Corcoran, Stamford, Conn.; Kenneth T. Chung, Greenlawn, N.Y.

[73] Assignee: Estee Lauder, Inc., New York, N.Y.

[21] Appl. No.: 293,416

[22] Filed: Aug. 19, 1994

Related U.S. Application Data

[63] Continuation of Ser. No. 23,498, Feb. 26, 1993, abandoned.

[51] Int. Cl.$^6$ .............................. A61K 7/42; A61K 47/00
[52] U.S. Cl. ........................... 424/59; 514/772; 514/784; 514/785; 514/786
[58] Field of Search ..................... 424/59; 514/772, 514/784, 786, 786

[56] References Cited

U.S. PATENT DOCUMENTS

| | | | |
|---|---|---|---|
| 4,927,464 | 5/1990 | Cowie | 106/436 |
| 5,028,417 | 7/1991 | Bhat et al. | 424/59 |
| 5,032,390 | 7/1991 | Iwaya et al. | 424/59 |
| 5,188,831 | 2/1993 | Nicoll et al. | 424/63 |

FOREIGN PATENT DOCUMENTS

| | | |
|---|---|---|
| WO90/06103 | 6/1990 | European Pat. Off. . |
| 2206282 | 1/1989 | United Kingdom . |
| 2206339 | 1/1989 | United Kingdom . |
| 2217987 | 11/1989 | United Kingdom . |
| 2226018 | 6/1990 | United Kingdom . |

OTHER PUBLICATIONS

Alexander, P., "Ultrafine Titanium Dioxide Makes the Grade", *Manufacturing Chemist* 62(7):21–23 (1991).

Fox, C., "Cosmetic Raw Materials: Literature and Patent Review 1989–1991", *Cosmetics & Toiletries* 106: 69–87 (1991).

Brown, M. W. and Galley, E., "Testing UVA and UVB Protection From Microfine Titanium Dioxide", *Cosmetics & Toiletries* 105: 69–73 (1990).

Fox, C., "Cosmetic Raw Materials: Literature and Patent Review 1988–1990", *Cosmetics & Toiletries* 105: 77–96 (1990).

Diffey, B. L. and Robson, J., "A New Substrate to Measure Sunscreen Protection Factors Throughout the Ultraviolet Spectrum", *J. Soc. Cosmet. Chem.* 40: 127–133 (1989).

Klein, K., "Formulating Effective Yet Elegant Sunscreen Products", DCI, pp. 22–30 (Aug. 1989).

*Primary Examiner*—Raymond Henley, III
*Attorney, Agent, or Firm*—Pennie & Edmonds

[57] ABSTRACT

A novel organic dispersion comprises microfine titanium dioxide and a suitable branched chain organic without the use of any dispersing agent. The novel dispersion provide uniquely high SPF with low levels of dry weight titanium dioxide. Methods for preparing said dispersion and cosmetic sunscreen compositions comprising said dispersion are also included within the invention.

13 Claims, No Drawings

TITANIUM DIOXIDE DISPERSIONS, COSMETIC COMPOSITIONS AND METHODS FOR USING SAME

This is a continuation of application Ser. No. 08/023,498 filed Feb. 26, 1993, now abandoned, which is incorporated by reference herein in its entirety.

FIELD OF THE INVENTION

The present invention relates to a novel organic dispersion of titanium dioxide particles suitable for use in sunscreen preparations. The invention further relates to the preparation of said titanium dioxide dispersion and to methods for employing said dispersion in cosmetic sunscreen compositions. Finally, the invention relates to methods for using cosmetic sunscreen preparations containing said titanium dioxide dispersion.

BACKGROUND OF THE INVENTION

Sunscreens are cosmetic compositions which are applied topically to human skin to provide protection against the harmful ultraviolet rays of the sun (UV-A and UV-B radiation, generally in the range of 290–400 nm). Conventional sunscreens are prepared using cosmetically acceptable lotions, oils, creams, and emulsions (both oil-in-water and water-in-oil). Typically, organic agents have been employed in sunscreen compositions as the active ingredient. For example, PABAs (p-aminobenzoic acids), benzophenones, salicylate esters and dioxybenzone have been used. More recently, inorganic agents have been employed in sunscreen compositions. For example, zinc oxide, titanium dioxide, and calamine.

The inorganic agents, such as titanium dioxide, have a tendency to agglomerate which reduces their efficacy as UV screening agents in cosmetic sunscreen compositions. Additionally, sunscreen compositions containing titanium dioxide have an unpleasant feel on the skin of the user, particularly when higher concentrations of titanium dioxide are used. Further, the titanium dioxide sunscreens usually contain levels of the active ingredient which result in increasing whiteness/blueness on the skin, i.e., increased visible light opacity. Therefore, the cosmetic formulator is confronted with several problems when formulating sunscreen compositions employing titanium dioxide.

In general, formulation optimization, always a goal of the cosmetic formulator, for sunscreens (and sunblocks) aims for higher SPFs (Sun Protection Factor), mildness and water-resistancy. Ken Klein, DCI pp. 22–30, August 1989. Cosmetic formulators have had the option of using titanium dioxide as the active sunscreen ingredient since early 1978 when it was approved by the OTC Panel of the FDA for use in sunscreen preparations. Nevertheless, the problems mentioned above have persisted.

The grade of titanium dioxide used in cosmetics, particularly as sunscreens, is different than that used as a pigment in the paint, paper and plastics industries. The most distinct difference is that of particle size. The particle size of titanium dioxide used as a pigment is such that its use in cosmetics is limited by the increase in whiteness on the skin.

Schwartz and Peck reported in 1947 that heavily pigmented preparations (liquids, creams or powders) will prevent or reduce the passage of the UV radiation, but while preventing sunburn, such preparations will also prevent suntan. Zinc oxide, calamine and titanium dioxide are the most effective in this regard. *Cosmetics & Dermatitis* 1947, Paul B. Hocker, New York, 145. Again, an ideal sunscreen requires the ability to attenuate both UVA and UVB radiation, while being chemically inert, non-toxic, non-irritating and non-sensitizing.

Brown and Galley have reported that the appropriate UV opacity can be maintained by titanium dioxide particle sizes as small as 100 nm and less (microfine or ultra-fine) while reducing visible light opacity, thus making titanium dioxide cosmetically acceptable. *Cosmetics & Toiletries* 105: 69–73 (December 1990). They also reported that titanium dioxide particle sizes, selected to have acceptable cosmetic properties, can still exhibit broad spectrum activity, offering protection to both UVB and UVA wavelengths, unlike organic sunscreens which are generally either UVA or UVB specific. Id.

Clearly, there was a breakthrough in cosmetic technology when it was discovered that if titanium dioxide was produced in an ultra-fine form (microfine), it was possible to obtain transparent films on the skin. However, the degree of protection conferred to the user would depend on the concentration of the ultra-fine titanium dioxide in the sunscreen preparation. Generally, to achieve high SPF (Sun Protection Factor) values, higher concentrations of titanium dioxide are needed which returns one to the problem of whitening color on the skin and unpleasant or grimy feels. (See Diffey and Robson, *J. Soc. Cosm. Chem.*, 40: 127–133 (May–June 1989) for a system for testing SPF's both in UVA and UVB regions.) Philip Alexander reports that 1% of ultra-fine titanium dioxide, as the active sunscreen agent, in a sunscreen product would give an SPF of between 2 and 3. *Manufacturing Chemist* 62(7): 21 (July 1991).

Titanium dioxide has been described in the literature as a brilliant white, amorphous and odorless powder. It is found in nature as the minerals rutile and anatase. Philip Alexander has reported titanium dioxide to be insoluble in water and in fatty acid esters in which it disperses. *Manufacturing Chemist* 62(7): 21 (July 1991).

Ultra-fine titanium dioxide is available commercially from several vendors for cosmetic use. Titanium dioxide is available with either an inorganic or organic coating. Aluminum stearate and aluminum oxide coatings are common inorganic coatings. Aluminum laurate and aluminum hydroxide are also used as coatings on titanium dioxide. In addition, Tioxide Chemicals, U.K. manufactures several grades of ultra-fine titanium dioxide which are surface treated and dispersed in a variety of organics, such as mineral oil/triglyceride, octyl palmitate and isopropyl myristate, using a dispersing agent.

Since the introduction of microfine titanium dioxide, there has been an increase in the use of titanium dioxide as a sunscreen. With the increase in experience with titanium dioxide, additional problems have arisen such as the observation that microfine titanium dioxide has a propensity to agglomerate (clump) into large particles. Several attempts have been made to remedy this and the other problems mentioned above, e.g., to produce new particle size titanium dioxide.

International Publication No. WO 90/06103, published Jun. 14, 1990 reports that coating titanium dioxide particles of a size less than 100 nm with phospholipids reduces their tendency to clump and enables the particles to be more effectively dispersed. It is reported that the enhanced dispersibility of the particles allows higher concentrations of titanium dioxide than were previously possible to be incorporated into stable fluid emulsions and dispersions. The enhanced dispersibility of the phosphorized coated particles is also alleged to improve UV screening efficiency.

U.K. Patent Application GB 2,226,018A, published Jun. 20, 1990 describes an aqueous dispersion of acicular fine particle size titanium dioxide (largest dimension is 0.01 to 0.15 microns) containing 20 to 60% by weight solids plus a polycarboxylic acid dispersant. The aqueous dispersion is milled to produce a product absorbent to ultra-violet (UV) light and substantially transparent to visible light.

U.S. Pat. No. 4,927,464 describes a form of titanium dioxide which is ocular in shape, having a ratio of the largest dimension to the shortest within the range 8:1 to 2:1 and wherein the largest dimension is from 0.01 to 0.15 microns and in which the particles have a coating of a hydrous oxide of aluminum and of silicon in a weight ratio of at least 1.5 and not greater than 4.5 expressed as the oxides.

U.K. Patent Application GB 2,206,339A describes a dispersion of titanium dioxide particles of size 0.01 to 0.15 microns employing an organic oil, such as vegetable oils, fatty alcohols, saturated fatty acid diesters and linoleic glycerides; and a dispersing agent based on one or more polyesters or salts of a hydroxycarboxylic acid and a carboxylic acid free of hydroxy groups. The U.K. patent application discloses that other suitable dispersing agents are monoesters of fatty acid alkanolamides and carboxylic acids and their salts based on 6–226 (un)saturated fatty acids. It is also reported therein that sunscreen preparations which contain these types of dispersions were prepared. The inventors of the U.K. patent application report that 12.5% w/w of the titanium dioxide dispersion (42% solids) gives a weighted cast SPF of 6; and a 25% w/w dispersion (42% solids) gives a weighted cast SPF of 7.3. Similarly, other sunscreen preparations containing 12.5% and 25% w/w of the titanium dioxide dispersion (42% solids) gave weighted cast SPFs of 9.3 and 10.8, and in vivo SPFs of 10.2 and 11.6, respectively.

As mentioned above, many cosmetic sunscreen preparations employing titanium dioxide as the active sunscreen, have been prepared. For example, U.S. Pat. No. 5,028,417 describes a sunscreen composition containing an extending medium and titanium dioxide having a particle size of less than 10 nm(mµ). Further, the U.S. Pat. No. 5,028,417 describes a dispersion formulation containing an 80/20 mixture of titanium dioxide with barium sulfate coated with stearic acid (62% titanium dioxide) dispersed in isooctyl stearate by means of a pearl mill (Dyno-Mill Type KDL). It is reported that the resulting dispersion contains 15.5% titanium dioxide and has an SPF of 14.6.

U.K. Patent Application GB 2,217,987A describes sunscreen compositions containing 0.5 to 30% by weight of titanium dioxide having a primary size of less than 100 nm and which is coated with aluminum stearate; 5 to 20% by weight of an oil phase; 1 to 15% by weight of an emulsifier; and at least 40% by weight of an aqueous phase.

From the above discussion, it should be apparent that inorganic sunscreen agents like ultra-fine titanium dioxide are superior to traditional organic sunscreen agents (less irritation potential and better/broader UV protection). Because of its unique properties, ultra-fine titanium dioxide is being increasingly used in cosmetic sunscreens today. Nevertheless, there are still many problems associated with the use of ultra-fine titanium dioxide. In particular, the level of ultra-fine titanium dioxide powder necessary to achieve proper (and higher) SPF levels makes the product aesthetically unacceptable, i.e., there is a heavy and draggy feel (which may also result in skin irritation) and a white/blue residual on the skin. Similarly, commercially available ultra-fine titanium dioxide has a propensity to agglomerate into clumps of much higher particle sizing. Use of such agglomerations is unacceptable for cosmetic sunscreens.

It is an object of the present invention to provide a novel dispersion of titanium dioxide, without the use of any dispersing agent, which achieves higher SPF levels with lower levels of titanium dioxide.

It is also an object of the present invention to provide cosmetic sunscreen compositions with proper SPF levels while eliminating the unacceptable heavy feel, residual color and other undesirable properties associated with certain levels of titanium dioxide.

Further, it is an object of the present invention to provide a process for dispersing ultra-fine titanium dioxide particles prior to utilization in cosmetic sunscreens.

It is yet a further object of the present invention to provide cosmetic sunscreen compositions which do not utilize organic sunscreens and have high SPF while maintaining good feel and transparency.

SUMMARY OF THE INVENTION

It has been discovered that certain grades of ultra-fine titanium dioxide can be combined with certain branched chained organic compounds to form a dispersion which achieves much higher levels of SPF using significantly low levels of titanium dioxide. The novel dispersions of the present invention enable one to formulate cosmetic sunscreen compositions that have excellent aesthetics heretofore unachievable.

The present invention encompasses an organic dispersion of microfine titanium dioxide comprising coated or uncoated titanium dioxide of a particle size, prior to any agglomeration, of about 10 nm to about 100 nm; and a suitable branched chained organic compound without the use or employment of any dispersing agent. The organic dispersions of the present invention are prepared by subjecting the microfine titanium dioxide and the suitable branched chained organic compound to a ball mill, roller mill or ultrasonic mixer. In general, once the titanium dioxide has been dispersed in the suitable branched chained organic compound, it is ready for use in cosmetic sunscreen preparations as the active sunscreen ingredient.

It has been unexpectedly discovered that the novel organic dispersions of the present invention achieve high SPF values with low levels of dry weight titanium dioxide powder. This allows for a more cost effective and less irritating cosmetic sunscreen while exploiting the excellent sunscreen properties of microfine titanium dioxide.

The present invention also encompasses a cosmetic sunscreen preparation which comprises an effective amount of an organic dispersion described above as the active ingredient. These cosmetic sunscreen preparations generally comprise about 1 to about 50% of the organic dispersion, wherein said sunscreen preparations comprise about 0.4 to about 25% dry weight microfine titanium dioxide.

Finally, the invention encompasses a method of dispersing microfine titanium dioxide and a suitable branched chained organic compound without the use of a dispersing agent, such that higher SPF values can be achieved with lower levels of dry weight microfine titanium dioxide.

DETAILED DESCRIPTION OF THE INVENTION

Certain grades of ultra-fine (microfine) titanium dioxide can be combined with a suitable branched chained organic compound without the use of a wetting or dispersing agent to form a novel dispersion which achieves much higher levels of SPF using significantly low levels of titanium dioxide. These grades of ultra-fine or microfine (these terms are used synonymously herein), include both uncoated and coated titanium dioxide of a particle size of about 10 nm to about 100 nm. The particle size refers to the titanium dioxide particle size prior to any agglomeration which may occur during storage or transportation. It is preferred that the titanium dioxide is coated with, for example, an inorganic coating such as aluminum laurate and aluminum hydroxide; however, other coatings both inorganic and organic known to those skilled in the art can also be utilized. It is also preferable that the particle size of titanium dioxide be from about 10 nm to about 50 nm; and most preferably about 15 nm to about 25 nm.

The organic dispersion of the present invention is prepared from the microfine titanium dioxide discussed above, and a suitable branched chained organic compound. It has been discovered that the suitable branched chained organic compounds of the present invention form a dispersion with the microfine titanium dioxide without the use of a dispersing agent. Further, the novel dispersions are extremely useful in cosmetic sunscreen preparations because they achieve high levels of SPF using low levels of titanium dioxide. This can be seen in Examples 5 and 6, infra. These examples demonstrate that an organic dispersion which contains 20% less microfine titanium dioxide yields a comparable SPF value to that of an undispersed microfine titanium dioxide composition. Similarly, the microfine titanium dioxide organic dispersion of the present invention was compared to that of Tioveil Fin® (Tioxide). Tioveil Fin® is a preformed microfine titanium dioxide dispersion which utilizes a dispersing agent. Equivalent amounts of this dispersion and that of the present invention were tested for SPF values using a procedure based upon the method outlined in the FDA monograph of proposed rules for sunscreen testing published in the Federal Register, Vol. 43 No. 166, Aug. 25, 1978. As can be seen in the examples, the dispersion of the present invention gave higher levels of SPF.

The ability to achieve higher levels of SPF with lower levels of microfine titanium dioxide allows one to formulate cosmetic sunscreen preparations which are less grimy and draggy, and thus more aesthetically acceptable. In addition, at higher SPF's the formulator will not have the problem of residual whiteness or blueness on the skin from high concentrations of titanium dioxide powder.

Suitable branched chained organic compounds within the scope of the present invention include cosmetically acceptable highly branched chained esters, fats and oils, fatty acids, ethers, glyceryl esters, hydrocarbons, lanolins and lanolin derivatives, and silicons or silanes, as well as combinations thereof. As used herein, the term "highly branched chained" means that the compound has a minimum carbon skeleton of 10 carbon atoms, which skeleton contains a number of hydrocarbon substituents. Suitable branched chained organic compounds include esters, such as, cetearyl isononanoate, decyl isostearate, dicetyl thiodipropionate, diglyceryl stearate maleate, dihydrocholesteryl octyldecanoate, diisopropyl dilinoleate, isodecyl neopentanoate, isopropyl isostearate, isostearyl isostearate, isostearyl stearoyl stearate, isotridecyl isononanoate, myristyl isostearate, myristyl neopentanoate, propylene glycol diisononanoate, triisopropyl trilinoleate and octyldodecyl neopentanoate. The preferred suitable branched chained organic is octyldodecyl neopentanoate.

Commercially available grades of microfine titanium dioxide have a tendency to agglomerate into particle sizes greater than 150 nm. Dispersing these particles in a suitable branched chained organic compound by milling or ultrasonic mixing, in accordance with the present invention, reduces the particle sizes, i.e., deagglomerates the titanium dioxide. In addition, the organic dispersion formed has unique SPF properties and cosmetic acceptability.

The present invention requires a certain grade of titanium dioxide, a suitable branched chained organic compound and a certain processing technique. The dispersions of the present invention can be prepared by roller milling, ball milling and ultrasonic mixing. These milling techniques and the equipment used therefor are well known to those skilled in the art. See for example Kirk-Othmer Encyclopedia of Chemical Technology 3rd Ed., John Wiley & Sons, Inc. 1984. The mills which are employed to effect the grinding of the titanium dioxide in the suitable branched chained organic compound is one which uses a particulate grinding medium to grind the product. Such mills are the various types of mills equipped with one or more agitators and using sand, glass or ceramic beads or other particles as the particulate grinding medium. The dispersions can also be premixed using a high speed stirrer prior to milling. In addition, an ultrasonic mixing instrument can be utilized, for example, a Sonicator Instruments Corp. Model UPP400. Suitable ball mills include the Premier SuperMill HM45. Suitable roller mills include Keith, Ross and Day brands.

Once the organic dispersion of microfine titanium dioxide and the suitable branched chained organic compound has been prepared, it can be used in a wide variety a cosmetic preparations. In particular, the organic dispersion has great utility in cosmetic sunscreen preparations as the active sunscreen agent. The organic dispersion can be used in emulsion systems (both oil-in-water and water-in-oil), creams, lotions and oils. Similarly, the organic dispersion can be used as a secondary sunscreen, e.g., used in combination with other category 1 sunscreen agents, although the unique properties of the dispersion of the present invention make such other sunscreens unnecessary. Examples of the use of the novel dispersions in cosmetic sunscreen preparations is given in the Examples, infra.

Generally, the organic dispersions of the present invention contain about 10% to about 80% microfine titanium dioxide. The organic dispersions prepared using an ultrasonic mixer can contain from about 0.5% to about 80% microfine titanium dioxide. In a preferred embodiment, the organic dispersion contains from about 15% to about 50% microfine titanium dioxide. In most preferred embodiments, the organic dispersion contains about 40% microfine titanium dioxide. The amount of the dispersion used in a cosmetic preparation will depend on the SPF value desired. Generally, for a SPF value of about 30, approximately 30% by weight of the composition is the organic dispersion. A composition containing 30% of an organic dispersion according to the present invention can have 12% dry weight microfine titanium dioxide (e.g., 30% by 40% microfine $TiO_2$). The cosmetic compositions within the scope of the present invention contain from 0.4% to 25% dry weight titanium dioxide.

The present invention further encompasses cosmetic sunscreen preparations comprising an effective amount of said organic dispersion. As mentioned above, the effective amount is dependent upon the desired SPF level.

The present invention also encompasses a method for protecting the human skin from harmful UV radiation which comprises applying to the skin to be protected, an effective amount of a cosmetic sunscreen preparation containing an organic titanium dioxide dispersion described herein.

The following examples are given to illustrate the scope of the present invention. Because these examples are given for illustrative purposes only, the invention should be not inferred to be limited to these examples.

EXAMPLES

Example 1

Preparation of a 40/60 Microfine Titanium Dioxide Organic Dispersion Using a Ball Mill Add octyldodecyl neopentanoate (Elefac I-205® (Bernel)) into an appropriate size stainless steel mixing container (60%). Insert a Hockmeyer Disperser or an equivalent. Slowly add (40%) microfine titanium dioxide (Micro LA-20®) to the octyldodecyl neopentanoate increasing the speed of the Hockmeyer Disperser as necessary to completely disperse microfine titanium dioxide the octyldodecyl neopentanoate. Note that proper agitation is achieved when a "doughnut" type of mixing is observed. The amount of octyldodecyl neopentanoate in the container should be one-half to three quarters of the container volume to allow for maximum mixing speed. When the phase is completely uniform, set up the Premier Ball Mill™ by turning on the air and cooling water to the jacket. The Mill Load is 80% glass beads 1.5 mm average size. Add the uniform phase to the Mill Hopper and turn the infeed pump on using 350 RPM setting. Jog the mill for five second intervals. When the product begins to exit the mill, set up for recycle. Continue adding material to the mill and turn the mill on. Set the disc peripheral speed to 2000 fpm. Record the time when product begins to exit the mill. Check the grind (dispersion) on a Hegman Gauge. It must read 7 or greater. When the grind (dispersion) is satisfactory, continue milling the phase into the appropriate storage containers. Before using the disperser particle size determination must be made. The particle size should be less than 10 microns.

| Sequence | Ingredient | Aprox. Weight % |
|---|---|---|
| (1) | Elefac I-205 | 1.00 |
| (1) | Protachem ISP | 5.00 |
| (1) | Finsolv TN | 5.00 |
| (1) | Silicone 556 Fluid | 3.50 |
| (2) | Natural Maskant PF 598/14 | 0.40 |
| (2) | Magnesium Stearate D-NF (Regular) | 2.00 |
| (2) | Talc 141 USP (Alpine) | 3.75 |
| (2) | Orgasol 2002 D Nat Cos | 1.25 |
| (3) | Titanium Dioxide Dispersion | 17.50 |
| (4) | Abil EM-90 | 2.00 |
| (4) | Abil WE-09 | 1.00 |
| (5) | Deionized Water | 49.50 |
| (5) | Disodium EDTA/Sequestrene NA2 | 0.10 |
| (5) | Sodium Chloride Granular USP | 0.70 |
| (6) | Emeressence 1160 (Rose Ether) | 0.70 |
| (6) | Methyl Paraben USP | 0.25 |
| (6) | 1,3 Butylene Glycol | 6.00 |
| (7) | Alumina Hydrate –36330 | 0.35 |

Example 2

A Cosmetic Sunscreen Preparation for the Body (SPF 15) Containing the Microfine Titanium Dioxide Dispersion A cosmetic sunscreen preparation was prepared using the organic titanium dioxide dispersion prepared in Example 1. The organic dispersion (17.5% by weight) was admixed with the above ingredients according to standard cosmetic formulation techniques. The composition was found to have an SPF value 15.

The cosmetic sunscreen preparation of the above example was prepared as follows. The ingredients of sequence 1 are weighed into a support kettle and propeller agitation is started (100–150 rpm). Heat to 40° C. Mix until all solids are dissolved and phase is clear. Stop heating. Increase the propeller agitation to create a vortex and sprinkle sequence 2 directly into the eye of the vortex. Lower the portable homogenizer into the support kettle and begin 1800–2200 rpm agitation. Mix until all solids are dispersed (15 min. minimum). Transfer sequences 1 and 2 to the main kettle and begin 6–10 rpm sidesweep agitation combined with slow speed turbo-sheer agitation (500–800 rpm). Avoid aeration. Slowly add sequence 3 grind increasing turbo sheer agitation as necessary to maintain good batch turnover without aeration. Mix for 20 min. or until uniform. Confirm that the combined Sequence 1–3 are uniform and well dispersed by putting a sample between glass slides and checking for undispersed specs. Add Sequence 5 (water phase) to the Support Kettle and mix under simultaneous 150–200 RPM propeller agitation and 1500–2000 rpm homogenization until the solids are dissolved and phase is uniform. Weight Sequence 6 into an auxiliary vessel equipped with propeller mixer. Mix until the solids are completely dissolved in the Butylene Glycol. When Sequence 5 solids are completely dissolved, add the Sequence 6 pre-mix and mix under 150–200 RPM propeller and 1500–2000 rpm homomixer agitation until uniform. Add Sequence 7 to the combined Sequences 5–6 and mix until uniform. After the 20 minute homogenization of combined Sequence 1–3 is completed, check that the phase is uniformly dispersed as above. Continue homogenizing until uniform, then stop the Turbo-shear homogenizer. Continue side-wiper agitation at 8–10 rpm. Add Sequence 4 to the Primary Kettle and mix under side-wiper agitation for 15 minutes or until combined Sequence 1–4 is uniform.

| BATCH SIZE (Kg) | SWEEP RADIUS (ft) | MIXER SPEED (RPM) |
|---|---|---|
| 250–400 | 1.375 | 18–24 |
| 900–1200 | 2.250 | 11–14 |
| 2000–3500 | 2.917 | 9–11 |

NOTE:
SIDE-WIPER MIXING SPEED RANGE IS DEPENDENT ON BATCH SIZE.

When Sequence 1–4 is uniform, very slowly transfer the combined Sequence 5–7 into the Primary kettle. Maintain side-wiper mixer speed indicated in note above. When done properly, this transfer will take no less than 1 hour and as much as 2 hours. When transfer is complete, maintain side-wiper mixing as in note above and use a spatula to work any remaining water phase into the batch. After the batch is uniform, mix for 15 minutes under side-wiper agitation. Set up to recirculate the batch from kettle bottom outlet back into the top of the kettle. After the 15 minute mix period, increase the Planetary side-wiper mixer by 2–4 RPM. Begin recirculating the batch and START the Turbo-shear homogenizer at 2500–2700 RPM. Homogenize the batch for 5 minute intervals to build viscosity. Stop the homogenizer, and continue recirculating and sweep mix 15 minutes. Sample the batch from top and bottom and check the viscosity of each. Repeat homogenization intervals until both top and bottom samples are above 100,000 CPS. Continue to recirculate and side-wipe mix the batch until top and bottom readings are within 15,000 CPS of each other. When the desired viscosity is obtained, stop mixing and remove batch from kettle by transfer pump into poly-lined storage containers. Do not use a nylon filter bag.

Example 3

A Cosmetic Sunscreen Preparation for the Face (SPF 15) Containing the Microfine Titanium Dioxide Dispersion

| Sequence | Ingredient | Approx. Weight % |
|---|---|---|
| (1) | Citmol 320 | 1.54 |
| (1) | Bernel Ester DOM | 1.25 |
| (1) | Shea Butter | 2.00 |
| (1) | Promulgen D-CG | 3.75 |
| (1) | Glyceryl Monostearate 24 SE | 1.50 |
| (1) | Brij 35 SP | 0.80 |
| (1) | Myrj 59 Flaked | 0.50 |
| (1) | Elefac I-205 | 8.25 |
| (2) | Talc 141 USP (Alpine) | 5.00 |
| (2) | Orgasol 2002 D Nat Cos | 2.50 |
| (3) | Titanium Dioxide Dispersion | 18.75 |
| (4) | Deionized Water | 16.21 |
| (4) | Sequestrene NA3T/Sequestrene NA3 | 0.10 |
| (4) | Emeressence 1160 (Rose Ether) | 0.50 |
| (4) | Sodium Dehydroacetate | 0.10 |
| (4) | Keltrol F (1% Aq. Dispersion) | 10.00 |
| (4) | Methyl Paraben USP | 0.30 |
| (4) | 1,3 Butylene Glycol | 5.00 |
| (4) | Veegum HV (4% Aq. Dispersion) | 18.00 |
| (5) | Dow Corning 344 Fluid | 2.25 |
| (6) | Natural Maskant PF 598/14 | 0.40 |
| (7) | Germall 115 | 0.30 |
| (7) | Deionized Water | 1.00 |

A cosmetic sunscreen preparation for use on the face was prepared using the organic titanium dioxide dispersion of Example 1. The organic dispersion (18.75% by weight) was admixed with the above ingredients according to standard cosmetic formulation techniques. The composition was found to have an SPF of 15.

The composition was prepared as follows. Weigh Sequence 1 into the support kettle. Heat to 83° C. and start propeller mixer as soon as waxes have melted enough for it to turn. Adjust mixer to 170–220 rpm. When Sequence 1 is completely liquid, insert homogenizer and start homogenizing at 1800–2200 rpm. Add the powders of Sequence 2 into the support kettle using good agitation to wet out and disperse them. When Sequence 1 and 2 is at 83° C., add the Sequence 3 grind and homogenize for at least 20 minutes or until phase is uniform under 170–220 RPM propeller and 1800–2200 Rpm homogenizer agitation. Maintain 83° C. temperature. Confirm that combined sequences 1–3 are uniform and well dispersed by putting a sample between glass slides and checking for undispersed "specs". Weigh Sequence 4 into the Primary Kettle and start SLOWLY heating to 80° C. under 200–240 RPM propeller agitation. Heat sequence 4 slowly by throttling steam valve, or reducing steam pressure to primary kettle jacket. When combined Sequence 1–3 is uniformly dispersed, stop the homomixer and move it to the Primary Kettle. Start homogenizing Sequence 4 in the Primary Kettle at 2900–3600 rpm. Scrape side walls with spatula to minimize amount of veegum on sides of kettle. Make sure batch is lump free before adding Sequence 1–3. Remove steam from kettle jacket so no more veegum will burn on sides. Slowly transfer the combined Sequence 1–3 at 83° C. (Do not use Nylon Bag) to Sequence 4 at 80° C. over a 12 to 18 minute period under 250–300 rpm propeller and 2900–3600 rpm homogenizer agitation. When batch is uniform, stop and remove homogenizer. Increase propeller agitation to maintain a good rolling action (350–400 rpm), and cool the batch to 70° C. at a rate of about ½° C. per minute. At 70° C., add Sequence 5 to the batch. Increase propeller agitation as required to maintain a good rolling action (430–470 rpm) and continue cooling to 45° C. When batch becomes too thick for the prop to move (this occurs at 54°–62° C.), stop propeller mixer and remove it. Lower planetary mixer and start agitation at 8–10 rpm while continuing to cool batch to 45° C. At 45° C. maintain temperature, add Sequence 6 to the batch under 8–10 rpm sidewiper agitation. Resume cooling to 27° C. While the batch is cooling, prepare the Sequence 7 Germall solution in an auxiliary mixing vessel with propeller agitation. When Sequence 7 premix is completely uniform, add it to the batch at 35° C. Mix at least 15 minutes with 8–10 rpm side-wiper agitation while continuing to cool to 27° C. When batch is uniform and at 27° C. stop cooling and mixing. Remove batch from kettle by pumping slowly through a 150 mesh Nylon Bag (or equivalent) into poly-lined storage containers. Change nylon bag if clogging occurs.

Example 4

A Cosmetic Sunblock Composition for the Lips and Eye Areas (SPF-25) Containing the Titanium Dioxide Dispersion

| Ingredient | Approx. Weight % |
|---|---|
| Finsolv TN | 1.00 |
| Silicone 556 Fluid | 1.00 |
| Protachem ISP | 1.00 |
| Magnesium Stearate D-NF (Regular) | 2.00 |
| Titanium Dioxide Dispersion | 30.00 |
| Pure Oxy Red 3080-60% Protachem I | 0.15 |
| Cosmetic Yellow (40% in Protachem ISP) | 0.65 |
| Cosmetic Brown C33-115 in Protachem I | 0.12 |
| Abil EM-90 | 2.00 |
| Abil WE-09 | 1.00 |
| Deionized Water | 52.98 |
| Sodium Chloride Granular USP | 0.70 |
| Disodium EDTA/Sequestrene NA2 | 0.10 |
| Alumina Hydrate - 36330 | 0.35 |
| 1,3 Butylene Glycol | 6.00 |
| Emeressence 1160 (Rose Ether) | 0.70 |
| Methyl Paraben USP | 0.25 |

A cosmetic sunblock preparation was prepared using the organic titanium dioxide dispersion of Example 1. The organic dispersion (30.0% by weight) was admixed with the above ingredients according to standard cosmetic formulation techniques (see Example 2). The composition was characterized as an SPF value of 25.

Example 5

Comparison of the SPF Values Obtained with the Microfine Titanium Dioxide Organic Dispersion and Non-Dispersions

| | | SPF Found |
|---|---|---|
| Formula A | 15% TiO$_2$ (Micro LA-20) | >31.3 |
| Formula B | 15% TiO$_2$ (Micro LA-20) | >30.0 |

-continued

| | | SPF Found |
|---|---|---|
| Formula C | 15% TiO$_2$ (Micro LA-20) | 30.04 |
| Formula D | 30% of a 40/60 Titanium Dioxide Organic Dispersion (12% TiO$_2$) | >30.67 |
| Formula E | 30% of a 40/60 Titanium Dioxide Organic Dispersion (12% TiO$_2$) | >29.7 |

Several cosmetic compositions containing either 15% TiO$_2$ (MICRO LA-20®) or 30% of a 40/60 organic dispersion (12% TiO$_2$) prepared according to the procedure in Example 2 were prepared. The SPF values for each of these cosmetic compositions were determined according to the test method outlined below.

A. Procedure

Five (5) or twenty (20) panelists who met the inclusion criteria were selected for participation in this study.

Light Source—A Xenon Arc Solar Simulator (150 w) was used as the source of ultraviolet light. (Solar Light Company, Philadelphia, Pa.). The instrument produces a continuous emission spectrum in the UV-B range (290–320 nanometers).

Determination of Minimal Erythemal Dose (MED)—An MED is defined as the time interval or dosage of UV light irradiation sufficient to produce a minimal, perceptible erythema on untreated skin. Prior to the testing phase, the MED of each subject was determined by a progressive sequence of timed UV light exposures, each of which was graduated incrementally by 25% over that of the previous exposure. Sixteen to twenty-four hours after irradiation, the sites were evaluated for erythema according to the following scoring system:

0=Negative, no visible reaction

±=Minimal erythema

1+=Defined erythema

2+=Moderate erythema

3+=Severe erythema

Determination of Static SPF Values—A sufficient number of 5×10 cm test site areas were outlined with a surgical marking pen on the subject's back between the scapulae and the beltline, lateral to the midline. These areas were designated for the Test Article or Standard, with an adjacent site designated for a concurrent MED determination (unprotected control). After product application, each test area was subdivided into sites which were used for defined serial UV light exposure.

A 0.1 ml or 0.1 g portion of Test Article or Standard, was applied to the appropriate test site and spread evenly over the site using a fingercot. Irradiation of the sites was begun no less than 15 minutes and no longer than 30 minutes after application.

Exposure times were selected for each site in treated areas based upon the previously determined MED of unprotected skin and the anticipated SPF of the Test Article or Standard.

All test sites were evaluated 16 to 24 hours after exposure to determine minimal erythemal response.

Calculation of SPF—The SPF for the Test Article and Standard for each subjects was calculated according to the formula:

$$SPF = \frac{MED \text{ Test Article or Standard}}{MED \text{ Unprotected Control}}$$

Formula A included the following ingredients: Abil WE09, Finsolv TN, elefac I-205, hetester PHA, protachem ISP, Abil EM-90, TiO$_2$ LA-20, vitamin E acetate, Mg stearate, BHT, Finsolv TN, deionized water, NaCl, Na$_2$ EDTA, alumina hydrate, butylene glycol, Nayad and P-ethanol. Formula B included the following ingredients: BHT, Finsolv-TN, elefac 1–205, hetester PHA, protachem ISP, vitamin E acetate, magnesium stearate, TiO$_2$ LA-20®, cosmetic colorings, Abil Em90, deionized water, NaCl, Na$_2$ EDTA, alumina hydrate, butylene glycol, emeressence, and Nayad. Formula D included the following ingredients: protachem ISP, vitamin E acetate, magnesium stearate, BHT, silicone 556, Finsolv TN, TiO$_2$ organic dispersion of Example 1, cosmetic coloring, Abil EM-90, deionized water, NaCl, Na$_2$ EDTA, alumina hydrate, butylene glycol, P-ethanol and Nayad.

B. Results

The results in the Table above demonstrate that the novel dispersion of the present invention achieves a higher SPF with less dry weight titanium dioxide. In particular, the data shows that 12% dry weight titanium dioxide used in the dispersion achieves an SPF comparable to 15% dry weight titanium dioxide not used in a dispersion.

Example 6

Comparison of the SPF Value Obtained with the Microfine Titanium Dioxide Organic Dispersion of the Present Invention and that of a Tioveil Fin® (Tioxide, UK) Dispersion

| | | SPF Found |
|---|---|---|
| Formula A | 25% of a 40/60 Titanium Dioxide Organic Dispersion (10% TiO$_2$) | 23.00 |
| Formula B | 25% Tioveil Fin ® (40/60 Dispersion) Using C$_{12-15}$ Alcohol Benzoate (10% TiO$_2$) | 21.40 |

Two cosmetic compositions were prepared. Each had identical ingredients except for the dispersion used. One composition, Formula A, employed 25% of a titanium dioxide organic dispersion, prepared according to Example 2, which contains 40% titanium dioxide and 60% octydodecyl neopentanoate; thus, the dry weight titanium dioxide was 10% TiO$_2$. Formula B contains 25% Tioveil Fin® (Tioxide Chemicals, U.K.), a 40/60 dispersion prepared with C$_{12-15}$ alcohol benzoate and a dispersing agent. As can be seen from the example, the dispersion of the present invention provides a better SPF value than that of Tioveil FIN®.

It may be apparent to those skilled in the art that modifications and variations of the present invention are possible in light of the above disclosure. It is understood that such modifications are within the spirit and scope of the invention, which is limited and defined only by the appended claims.

What is claimed is:

1. An organic dispersion of microfine titanium dioxide comprising titanium dioxide selected from the group consisting of inorganically coated TiO$_2$, organically coated TiO$_2$ and uncoated TiO$_2$, of a particle size prior to agglomeration of about 10 nm to about 100 nm; and a cosmetically acceptable branched chained organic compound, without any dispersing agent; wherein said organic dispersion is formed by processing a mixture of said TiO$_2$ and said organic compound so as to effectively disperse said TiO$_2$ in said organic compound.

2. The organic dispersion of claim 1 wherein said particle size of titanium dioxide selected from the group consisting of organically coated TiO2, inorganically coated TiO2, and uncoated TiO2, prior to agglomeration, is about 10 nm to about 50 nm.

3. The organic dispersion of claim 2 wherein said particle size of titanium dioxide coated or uncoated, prior to agglomeration, is from about 15 nm to about 25 nm.

4. The organic dispersion of claim 1 wherein said cosmetically acceptable branched chained organic compound is a compound selected from the group consisting of cosmetically acceptable esters, cosmetically acceptable fats and oils, cosmetically acceptable fatty acids; cosmetically acceptable ethers; cosmetically acceptable glyceryl esters and derivatives, cosmetically acceptable hydrocarbons, cosmetically acceptable lanolin and lanolin derivatives, and cosmetically acceptable silicons and silanes, or combinations thereof.

5. The organic dispersion of claim 1 wherein said cosmetically acceptable branched chained organic compound is an ester selected from a group consisting of cetearyl isononanoate, decyl isostearate, dicetyl thiodipropionate, diglyceryl stearate malate, dihydrocholesteryl octyldecanoate, diisopropyl dilinoleate, isodecyl neopentanoate, isopropyl isostearate, isostearly isostearate, isostearyl stearoyl stearate, isotridecyl isononanoate, myristyl isostearate, myristyl neopentanoate, propylene glycol diisononanoate, triisopropyl trilinoleate and octyldodecyl neopentanoate.

6. The organic dispersion of claim 1 wherein said titanium dioxide is from about 10% to about 80% by weight of said dispersion.

7. The organic dispersion of claim 6 wherein said titanium dioxide is from about 15% to 50% by weight of said dispersion.

8. The organic dispersion of claim 7 wherein said titanium dioxide is about 40% by weight of said dispersion.

9. A cosmetic sunscreen preparation comprising an effective amount of an organic dispersion according to claim 1 as the active sunscreen ingredient.

10. The cosmetic sunscreen preparation of claim 9 wherein said organic dispersion is from about 1% to about 50% by weight of said composition.

11. The organic dispersion of claim 1, wherein said processing is selected from the group consisting of roller milling, ball milling and ultrasonic mixing.

12. A cosmetic sunscreen preparation which comprises about 1% to 50% of an organic dispersion of microfine titanium dioxide, wherein said organic dispersion comprises about 10% to 80% microfine titanium dioxide selected from the group consisting of inorganically coated $TiO_2$, organically coated $TiO_2$, and uncoated $TiO_2$ and a cosmetically acceptable branched chained organic compound, wherein said dispersion is prepared by processing a mixture of said $TiO_2$ and said organic compound so as to effectively disperse said $TiO_2$ in said organic compound, without utilizing a dispersing agent.

13. A cosmetic sunscreen preparation which comprises about 0.4% to about 25% dry weight of microfine titanium dioxide which has been dispersed in an organic dispersion by processing a mixture of $TiO_2$ and a cosmetically acceptable branch chained organic compound so as to effectively disperse said $TiO_2$ in said organic compound, without the use of any dispersing agents.

* * * * *